United States Patent [19]

Xiao

[11] Patent Number: 5,537,247

[45] Date of Patent: Jul. 16, 1996

[54] SINGLE APERTURE CONFOCAL IMAGING SYSTEM

[75] Inventor: Guoqing Xiao, San Jose, Calif.

[73] Assignee: Technical Instrument Company, San Francisco, Calif.

[21] Appl. No.: 213,977

[22] Filed: Mar. 15, 1994

[51] Int. Cl.[6] .................................................. G02B 21/00
[52] U.S. Cl. ........................... 359/368; 359/227; 359/235; 250/201.3
[58] Field of Search .......................... 250/201.3, 201.4, 250/201.5, 559.42; 359/368, 235, 227, 740; 356/372

[56]     References Cited

U.S. PATENT DOCUMENTS

| | | |
|---|---|---|
| 3,013,467 | 12/1961 | Minsky . |
| 3,517,980 | 6/1970 | Petran et al. . |
| 3,547,512 | 12/1970 | Baer . |
| 3,926,500 | 12/1975 | Frosch et al. . |
| 4,062,623 | 12/1977 | Suzuki et al. . |
| 4,170,398 | 10/1979 | Koester . |
| 4,198,571 | 4/1980 | Sheppard . |
| 4,251,129 | 2/1981 | Suzuki et al. . |
| 4,689,491 | 8/1987 | Lindow et al. . |
| 4,884,880 | 12/1989 | Lichtman et al. . |
| 4,884,881 | 12/1989 | Lichtman et al. . |
| 4,919,516 | 4/1990 | Petran et al. . |
| 4,927,254 | 5/1990 | Kino et al. . |
| 4,965,441 | 10/1990 | Picard ................................... 250/201.3 |
| 5,022,743 | 6/1991 | Kino et al. . |
| 5,091,652 | 2/1992 | Mathies et al. . |
| 5,101,295 | 3/1992 | Lichtman et al. . |
| 5,132,526 | 7/1992 | Iwasaki .................................... 359/368 |
| 5,448,350 | 9/1995 | Kohno ................................. 250/559.42 |

*Primary Examiner*—David C. Nelms
*Assistant Examiner*—F. Niranjan
*Attorney, Agent, or Firm*—Flehr, Hohbach, Test, Albritton & Herbert

[57]     ABSTRACT

A confocal scanning imaging system utilizes only one aperture for both the incident light from the light source and return light from the object. To improve its performance, the aperture plate is tilted with respect to the incident light path, the surfaces are coated with anti-reflection coating, the surfaces are optically flat, and the size of the aperture is designed to act as a one-way spatial filter. Other devices may be strategically placed to minimize the negative effects from scattered light.

29 Claims, 7 Drawing Sheets

FIG.—4

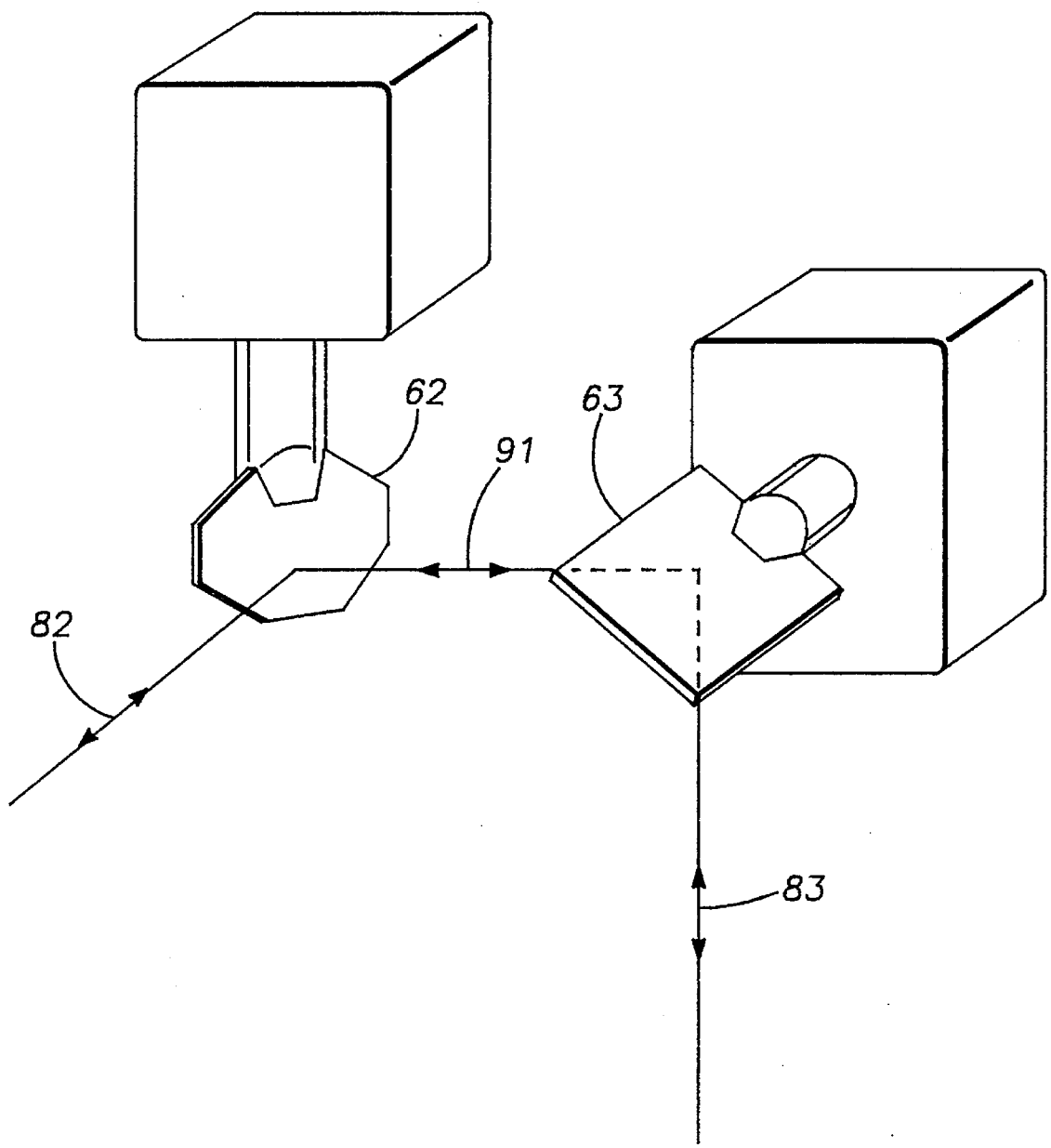
FIG.—7

SINGLE APERTURE CONFOCAL IMAGING SYSTEM

BRIEF SUMMARY OF THE INVENTION

The present invention relates generally to a confocal scanning imaging system and method, and more particularly to a confocal scanning imaging system with a single aperture for both the incident fight from the light source and return light from the object with filtering and a tilted aperture plate to minimize scattered and reflected light interference.

BACKGROUND OF THE INVENTION

Confocal scanning imaging systems are well-known in the art. Because of their ability to reject out-of-focus light and to image and reconstruct high resolution images of three-dimensional objects at all focal points on the object, they have been used in a wide variety of applications from industrial to biological technologies. High resolution is achieved by scanning the object in small increments at each x-y-z coordinate plane of focus.

The confocal imaging process is as follows. The confocal imaging system sequentially illuminates small focal regions of an object until the entire desired portion of the object is scanned. During the scanning process, reflected light from the small focal region is acquired. A user may view the image with a camera and display monitor. Additionally, the acquired image may be stored with an image processor and computer. A composite of all the small focal regions scanned results in a reconstructed image of the desired portion of the object itself with high resolution. Confocal imaging optically filters out light from regions outside the plane of focus at each small focal region to minimize scattered and reflected light interferences.

The use of apertures is essential to confocal imaging systems. The incident light illuminates only a small incremental focal plane or region on the object. In the return path, the aperture is located in a plane conjugate with the focal plane containing an image of the focal point on the object. Optical signals from out-of-focus points or regions are rejected because of the use of these apertures and the nature of the illumination. In other words, by strategically placing the aperture in a plane conjugate to the focal plane, only those return light emanating from the immediate vicinity or region of the illuminated focal point passes through the aperture and into the sensor for detection and processing.

Most confocal imaging systems utilize at least two apertures. One aperture is for the incident light from the light source to illuminate the incremental image point on the object. Another aperture is used for the return light from the incremental image point on the object. The apertures are of various shapes and sizes. The plate on which the apertures are located are either stationary or rotatable.

Various techniques are used to align or synchronize these two apertures as each incremental image point is obtained. Furthermore, optical designers and engineers constantly confront the problem of matching the size and shape of the incident and return light apertures. Confocal imaging systems employing two apertures are expensive, difficult to use, and need fine tuning and adjustments to obtain high resolution images. Merely changing the beam splicers and filters, as is often required in fluorescence applications, detrimentally affects the alignment of the imaging system.

The advent of single aperture confocal imaging systems appeared to eliminate some of the inherent problems associated with multiple aperture confocal imaging systems. After all, the use of one aperture for both the incident and return light seemed to eliminate alignment problems. However, image quality was not as superior as expected. One cause of this problem was the design of the size of the aperture. Although the aperture must be large enough to transmit all incident light from the light source, it should not be so large so as to accept all return light from the object and other scattered and undesired reflected light. Improper aperture sizes caused lower resolution images. Another cause of this problem was that the reflected light from the aperture itself is many orders of magnitude greater than the actual signal coming from the object, especially for fluorescence applications.

Other single aperture confocal imaging systems fail because of theft inability to shield crucial incident and return light paths from unwanted interference such as scattered and reflected light. Thus, image resolution is much lower than theoretically predicted.

One embodiment of the present invention minimizes these problems in a single aperture confocal imaging system by tilting the aperture plate, making the two major surfaces optically flat, coating the aperture plate with anti-reflection material, sizing the aperture so that it transmits all of the incident light while acting as a spatial filter for the return light, using a matching pre-conditioning aperture so that the light incident on the aperture plate is contained within the aperture of the aperture plate, or a combination of the above. Other devices such as filters, beam splitters, light stops, and lenses may also be utilized to reject, reduce, or redirect scattered and undesired reflected light.

In one embodiment, a laser is used as the light source. The advantage of using lasers is its use as an intense, monochromatic light source having a high degree of coherence. By scanning point by point with a laser beam, the temporal and spatial coherence is reduced at the field plane while remaining coherent in the aperture plane. Use of lasers in fluorescence applications is particularly useful. Embodiments of the present invention can generate clear, thin optical sections of fluorescence imaging system images without interference from out-of-focus fluorescence.

OBJECTS AND SUMMARY OF THE INVENTION

An object of the present invention is to utilize a single aperture for transmitting both incident light and return light in a confocal imaging system to facilitate ease of use, avoid alignment difficulties, and thus accelerate the imaging process.

Another object of the present invention is to make the single aperture optical system more effective by minimizing scattered and unwanted reflected light.

A further object of the present invention is to design the aperture plate so that it acts as a one-way spatial filter, and minimizing undesired plate surface reflections and interference between the two major plate surfaces.

The present invention is incorporated in a confocal scanning optical microscope where a single aperture is used for both the incident and return lights. To successfully implement such a system, interference from scattered and reflected lights is minimized by installing the single aperture plate at an angle, making the two major surfaces optically flat, coating the aperture plate with anti-reflection coating, sizing the aperture so that it acts as a one-way spatial filter only for the return light, using matching apertures to precondition the incident light before it reaches the aperture plate, and using filters, dichroic mirrors, and light stops. Scanning mirrors are used to produce a complete image of the object.

Use of the present invention in fluorescence applications offers a dramatic advantage by discriminating against out-of-focus background fluorescence, providing inherent resolution normal to the plane of focus, and providing improved in-plane resolution. Different ranges of fluorescence light are directed to different detection channels by using appropriate dichroic mirrors and filters.

BRIEF DESCRIPTION OF THE DRAWINGS

The foregoing and other objects will be more fully understood from the following detailed description read in connection with the accompanying drawings, of which:

FIG. 7 shows a close-up isometric view of the scanner and its image reflector plates used in the embodiment of FIG. 2.

DETAILED DESCRIPTION OF PREFERRED EMBODIMENTS

Figure 1:
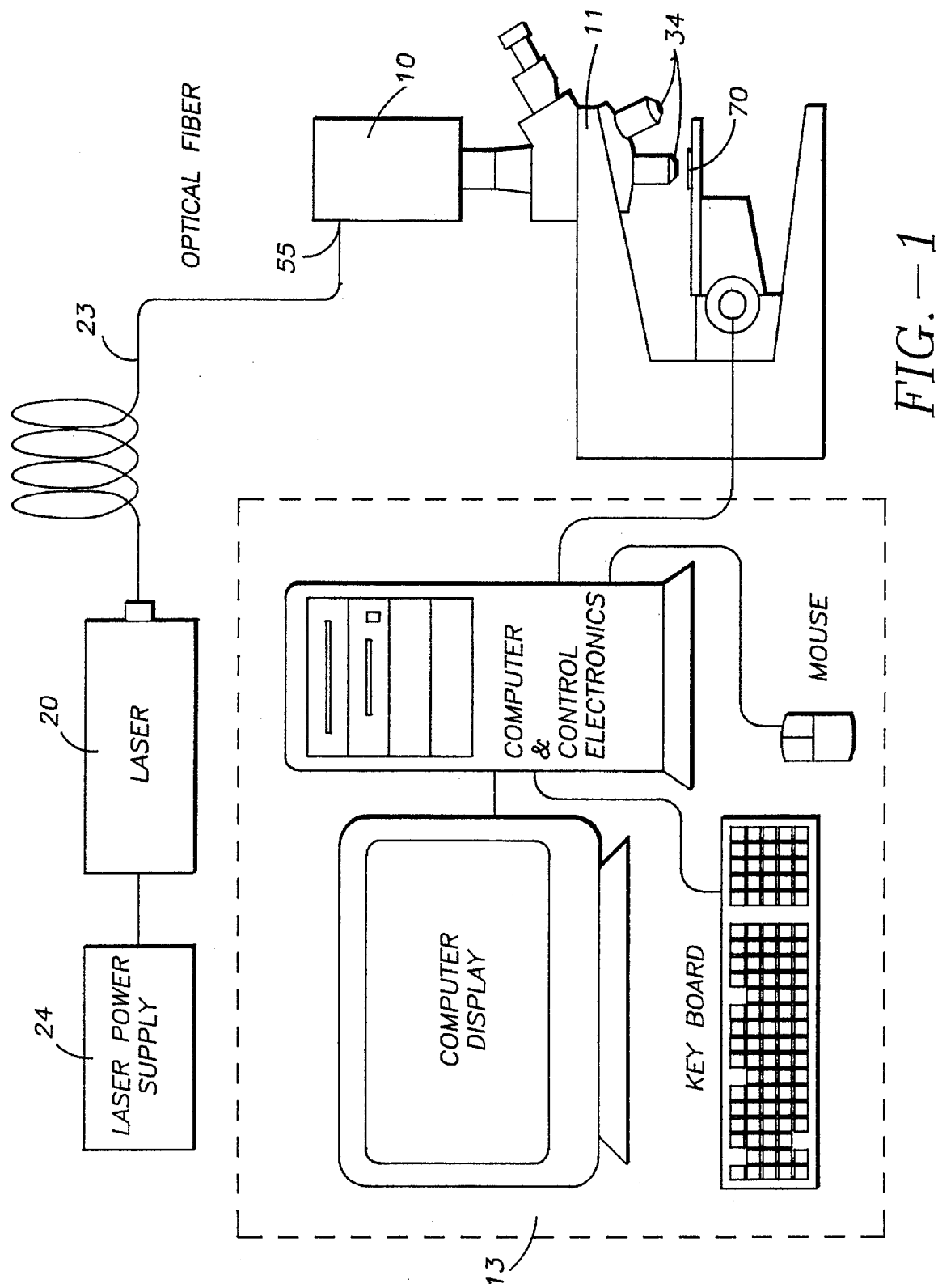
FIG. 1 shows an embodiment of the present invention incorporated in an optical system.

An embodiment 10 of the present invention is incorporated in the optical system of microscope 11 as shown in FIG. 1. Two well-known examples of microscope 11 are the Nikon Diaphot Inverted microscope and the Nikon Optiphot 2 microscope. The optical system includes a light source 20 such as a laser, a laser power supply 24 to power the laser, and an optical fiber 23 to guide the laser beam into microscope 11 through light entrance aperture 55. A computer system 13 provides processing and storage of the various x-y-z confocal images of object 70. The object 70 rests on movable mechanical translation stage 72.

Figure 2:
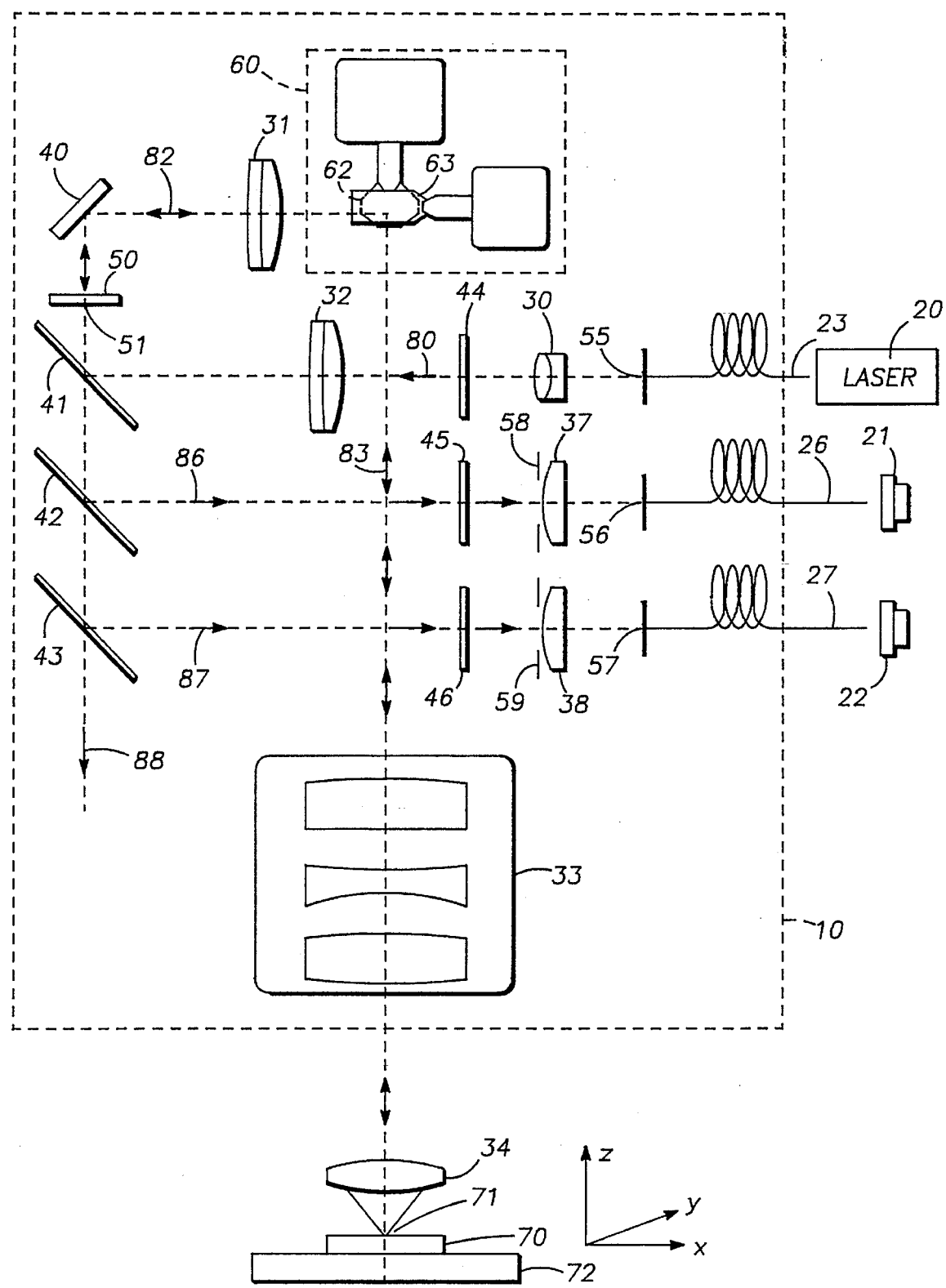
FIG. 2 shows the optical system in a preferred embodiment of the present invention. To change the image point on the object, a scanner and the translation stage is used.

FIG. 2 will be used to describe the operation of an embodiment of the present invention. Use of light paths 80–88 will facilitate the understanding of the discussion. Light source 20 provides the necessary light to illuminate each x-y-z image of object 70. Usually, the light from the light source is made up of more than one wavelength. The light source may be a laser, a Xenon arc lamp, or any other well known light source.

Light from the light source 20 travels to light entrance aperture 55 through optical fiber 23. Optical fiber 23 may be a single-mode optical fiber. Thus, light exiling the optical fiber 23 has a well-defined far-field distribution. Optical fiber 23 acts as a natural spatial filter; therefore, light entrance aperture 55 becomes redundant. The optical fiber 23 also serves as a transmission medium to guide the light from a remote location, if desired, to the optical system. By locating the light source 20 remotely, heat generated by the light source 20 does not affect the performance of the system.

The first light path 80 is between light entrance aperture 55 and dichroic mirror, or beam splitter, 41. After the light is pre-conditioned at light entrance aperture 55 or at the output of optical fiber 23, it then travels to collimating lens 30 which transforms the light so that the light beams run parallel to each other. These parallel light beams encounter an excitation filter 44. In other embodiments, the collimating lens 30 may be replaced with a cylindrical lens to accept light from a pre-conditioning slit aperture serving as light entrance aperture 55.

The excitation filter 44 passes light of only a range of pre-determined wavelengths. The type of excitation filter used dictates the wavelength or wavelengths passed. Focusing lens 32 focuses the light toward a beam splitter 41. The beam splitter 41 reflects incident light with a particular wavelength toward aperture plate 50 while transmitting along light path 84 return light, such as fluorescent light from the object, with a different range of wavelengths. In another embodiment, the excitation filter 44 may be replaced by a polarizer.

Figure 3:
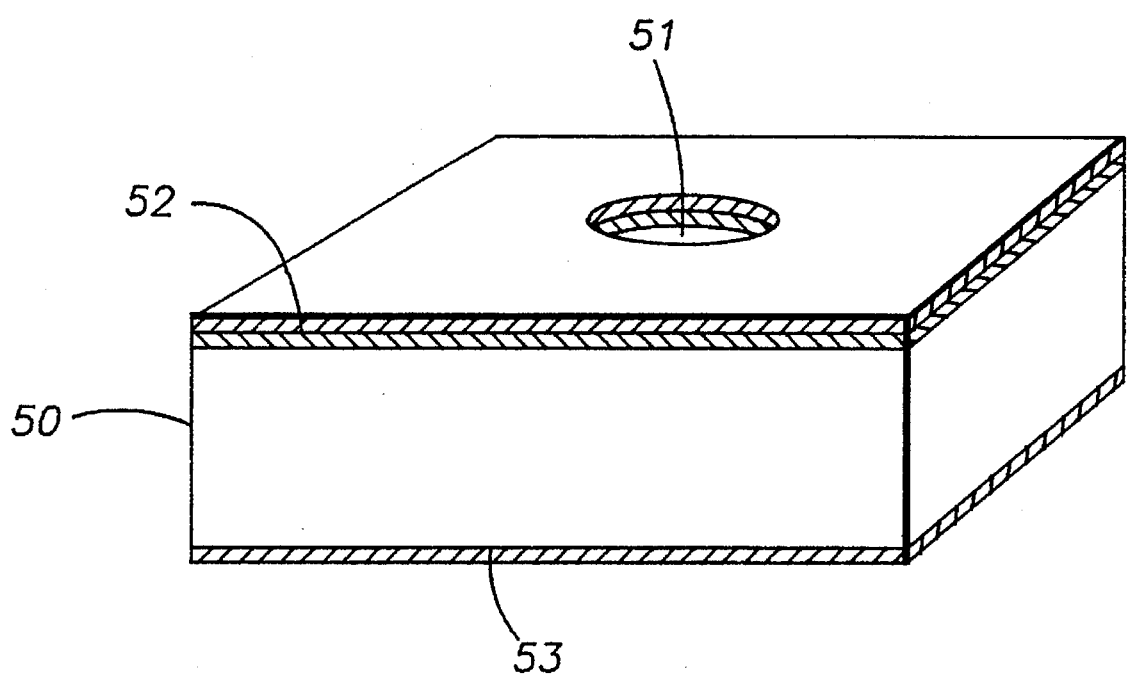
FIG. 3 shows an enlarged view of the aperture plate.

The beam splitter 41 directs the focused light toward aperture 51 on aperture plate 50 along light path 81. FIG. 3 shows an enlarged view of the aperture plate 50. In this embodiment, the aperture plate 50 is made of a transparent substrate, such as glass, coated on one side 52 with an opaque film such as chromium or aluminum. A clear region 51 which will serve as an aperture on aperture plate 50 is patterned on the film. Light can pass only through the clear region of the aperture plate 50. Thus, in this embodiment, light passes through the transparent substrate in order to pass the aperture. In other embodiments, the aperture may be a hole in the physical aperture plate.

As explained below, the two surfaces of the aperture plate 50 must be optically flat to control undesired reflections from the surfaces. The two surfaces should also be unparallel to minimize interference between the surfaces. The clear aperture can be of different shapes for different applications such as a circular pinhole, rectangular hole, a slit, or any desired shape.

To reduce the reflection from the aperture plate 50, light entrance aperture 55 must match the clear region, aperture 51, of the aperture plate 50 so that an image of aperture 55 forms within the aperture 51. Thus, minimum light is reflected from the opaque region of the aperture plate 50 and maximum light passes through aperture 51.

Light then travels to reflecting mirror 40 which is angled to direct the light toward the Galvanometer scanner 60 along light path 82. Along light path 82, light passes through collimating lens 31 toward Galvanometer scanner 60. In particular, light travels toward two scanning image reflector plates 62 and 63. As shown in FIG. 7, the orientation of image reflector plates 62 and 63 with respect to the light and to each other determines the precise x-y (z is constant) image coordinate scanned. The light paths 82 and 83 are as shown in FIG. 2. However, the spacing and the angular orientation of the image reflector plates 62, 63 create another light path 91. By rotating image reflector plate 62 (with plate 63 in a constant orientation), the image point 71 on the object 70 may be varied along the y-axis. Similarly, by rotating image reflector plate 63 (with plate 62 in a constant orientation), the image point 71 on the object 70 may be varied along the x-axis.

To scan along the z-axis, the embodiment of FIG. 2 shows that the mechanical translation stage 72 may be moved up or down to change the location of the image point 71 on the object 70. Thus, the scanner 60 and the translation stage 72 may be used to position the x-y-z coordinates of the image point 71 on the object 70. In another embodiment, the objective 34 may be moved up or down to change the location of the image point 71 on the object 70. In still another embodiment, the translation stage alone, without a scanner, can be moved laterally and vertically to locate the image point 71 on any practically realizable x-y-z coordinate on the object 70.

Along light path 83, the image reflector plates 62 and 63 direct light toward scan lens 33, objective 34, and object 70. Because the light is focused on an image point 71 on the object 70, an image of that image point 71 on the object 70 may be acquired and stored.

Light reflected or returning from image point 71 on the object 70 travels back along light path 83 via objective 34 and scan lens 33. The image reflector plates 62 and 63 of the scanner 60 redirect the light toward the reflecting mirror 40 through collimating lens 31 along light path 82. Reflecting mirror 40 directs the light toward aperture 51 on aperture plate 50 along light path 81. Note that in addition to the return light from the object, this aperture 51 was used to pass incident light from light source 20. By using the same aperture for both the incident and return light, this design facilitates ease of operation and eliminates difficult alignment procedures typically associated with multiple aperture confocal imaging systems.

Because of the ease of alignment of this single aperture system, several apertures 51 of different sizes or shapes may be mounted on a sliding mechanism such as a dovetail slider and thus allow users to switch among these apertures without realignment. Furthermore, several beam splitters of different spectral characteristics may be mounted on a sliding mechanism and thus allow users to switch among these beam splitters without additional alignment.

Light then travels through the beam splitter 41 along light path 84. Beam splitter 42 directs a portion of the light along light path 86 and another portion along light path 85. Similarly, beam splitter 43 directs a portion of the light from the beam splitter 42 toward the direction along light path 87 and another portion of the light, if desired, may be directed along light path 88. Several beam splitters may be installed in a cascade fashion, if desired, by placing them along light path 88. Beam splitters 42 and 43 each divide the incident beam of light into two beams of equal or different spectral composition but propagating in two different directions.

Light traveling along light paths 86 and 87 encounter barrier filters 45 and 46, respectively, where only a certain range of wavelengths passes through. For example, although light with wavelength 488 nm pass through excitation filter 44, only light with wavelengths 520–560 nm pass through barrier filter 45 and light with wavelength greater than 580 nm pass through barrier filter 46. The light passing through filters 45, 46 are focused by lenses 37, 38, pre-conditioned by light exit apertures 56, 57 and then collected by sensors 21, 22. The scattered light from the aperture plate 50 is significantly removed by light stops 58, 59.

If the sensors 21 and 22 are installed external to the imaging system, multimode optical fibers 26 and 27 may be used to guide and transfer the light to these sensors. In any event, the finite size of the optical fibers 26 and 27 also serves as an aperture to reject scattered light from the system. By using optical fibers 26 and 27, light stops 58, 59 become redundant. The sensors 21 and 22 may be placed close to the electronic portions of the system to minimize electronic noise. Light exit apertures 56, 57 or the input ends of optical fiber 26, 27 are matched to aperture 51 so that images formed in aperture 51 also form within light exit apertures 56, 57 or the input ends of optical fibers 26, 27. As a result, maximum signal reaches sensors 21, 22 and minimum scattered light passes through.

The use of barrier filters 45 and 46 are particularly useful in fluorescence applications. Fluorescent material emits radiation of a particular wavelength or range of wavelengths when it is excited by an incident energy. The wavelength of the incident energy is normally different from that of the fluorescent light. Thus, when portions of object 70 are coated or injected with one or more fluorescent material, incident light from image reflector plates 62 and 63 traveling toward object 70 may have wavelength of 488 nm, but the return fluorescent light from the object 70 may have a wavelength of, for example, 520–560 nm. If different fluorescent materials were used on the same object 70, the returning fluorescent light will possess the wavelengths for each of the fluorescent materials.

For these fluorescence applications, the use of an excitation filter, a dichroic minor (or beam splitter), and a barrier filter along light paths 86 or 87 of FIG. 2 can be used to further reduce the scattered light from the aperture plate 50. The parameters of the excitation and barrier filters are selected so that minimal overlap between the transparent spectral regions of the two filters exist.

Figure 4:
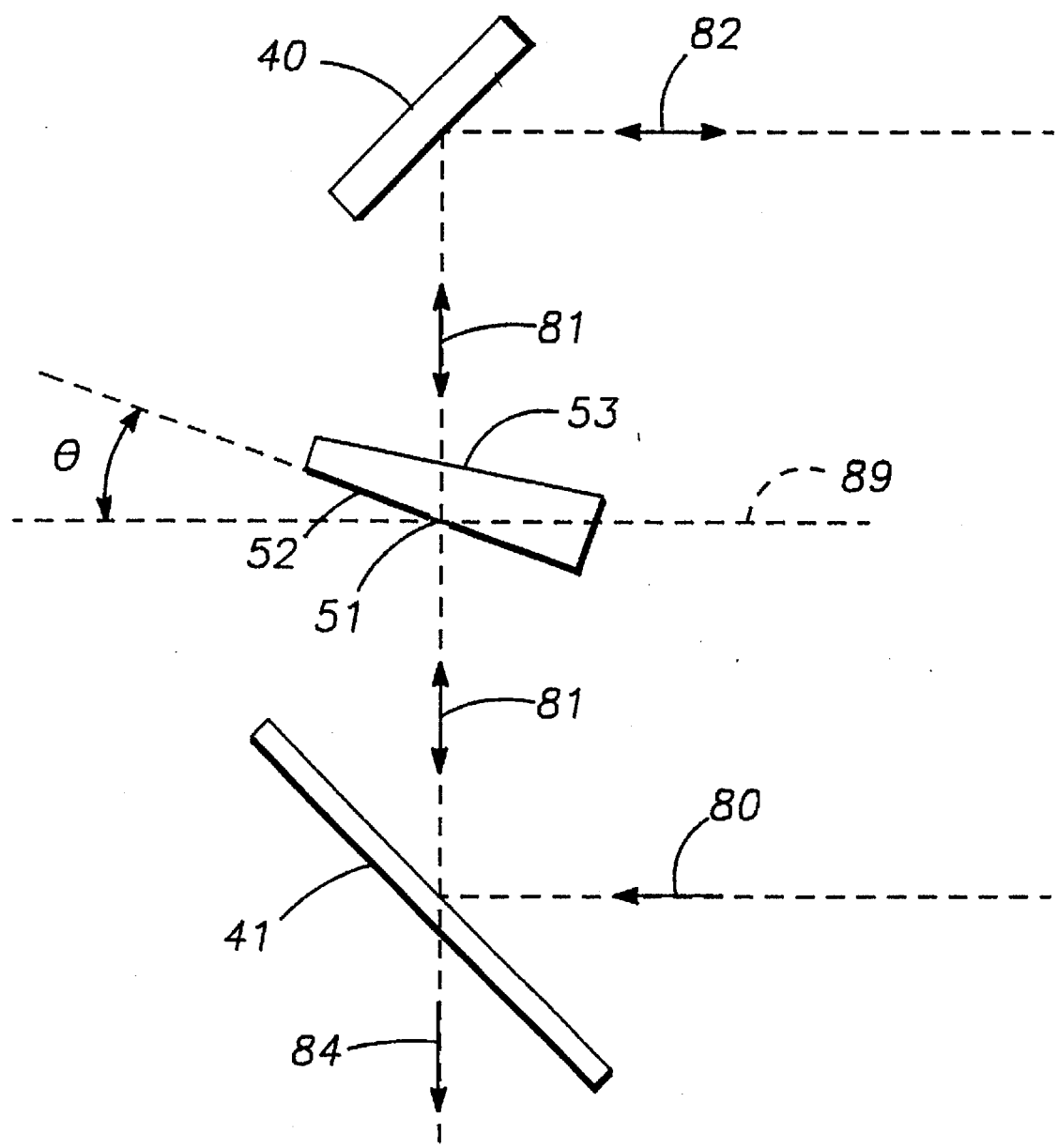
FIG. 4 shows another embodiment of the single aperture portion of FIG. 2.

To reduce the negative effects on image resolution from scattered and reflected light from sources other than the image point 71 on object 70, various improvements and variations of the optical system of FIG. 2 may be made. In one embodiment as shown in FIG. 4, the aperture plate 50 may be tilted at an angle θ from a plane normal to light path 81. This minimizes interference due to reflection from the surface of the aperture plate 50. Thus, little reflected light from the surface of the aperture plate 50 is directed toward beam splitter 41 and light path 84 to interfere with the desired returning light of the image point 71 on the object 70 of FIG. 2. With the aid of the tilt, any further reflection from the surface of the aperture plate can now be blocked with a light stop. The angle θ must not be too high, such as 90 degrees, or else useful light could not pass through the aperture 51. Furthermore, the angle θ should not be too low, such as 0 degrees, and thus defeat the purpose of the fit. A typical angle is between 3 to 6 degrees.

Figure 5:
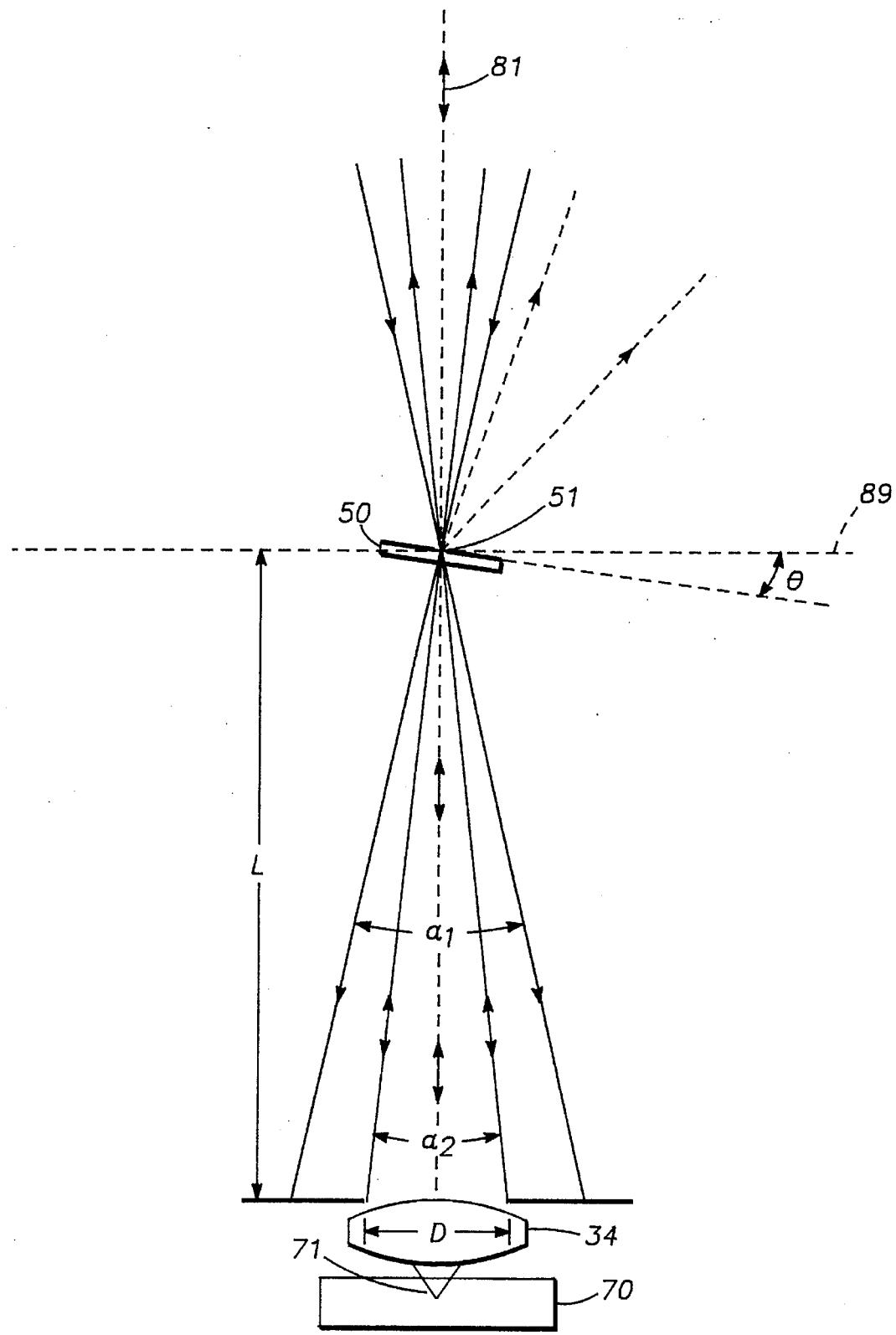
FIG. 5 is a further embodiment of the present invention showing the single aperture and the tilt angle.

In another embodiment shown in FIG. 5, one method of calculating the tilt angle θ is as follows. Let D represent the diameter of the entrance pupil of the objective lens 34 and L represents the distance from the intersection of fight path 81 with the plane 89 normal to the light path 81 at the location of aperture 51. Then, $$\alpha_2 = \frac{D}{L}$$

where $\alpha_2$ is the subtense angle of the entrance pupil of the objective lens to the aperture plate 50. The angle θ should be:

$$90° > \theta > \frac{1}{4}(\alpha_1 + \alpha_2)$$

where $\alpha_1$ is the convergent angle of the incident beam on the aperture plate.

The size of the aperture 51 on aperture plate 50 is also an important parameter in reducing the negative effects of interference from scattered and reflected light. The various filter, lens, and beam splitters along light path 80 provide the spatial filtering, shaping, pre-conditioning, or a combination thereof for a high numerical aperture (N.A.) to focus the incident light to a diffraction-limited spot within aperture 51. This spot is significantly smaller than the size of the aperture 51. Thus, the incident light may pass through the aperture 51 without any obstruction.

For the returning light, however, if the aperture 51 is too large, more scattered and reflected light will pass through the aperture and eventually to the sensor at the expense of image resolution. Accordingly, the N.A. of the return light path is designed to be smaller so that a minimum amount of undesired light can be reflected back from the object 70 (and other pans of the optical system) to the aperture 51. Thus, the focused spot is comparable to or larger than the size of the aperture 51. Accordingly, the aperture acts as a one-way spatial filter in the return light path.

The lateral $\Delta r_i$ extension of the illumination energy distribution in focus, or the focal spot size, and its dependence on the numerical aperture (N.A.) is given by the well-known relation:

$$\Delta r_i = \frac{0.61\lambda}{n\sin\left(\frac{\alpha_2}{2}\right)}$$

where, n=refractive index of the medium

λ=wavelength of incoming light $\alpha_2/2$=maximum half-angle with respect to the axis of the incoming light path.

Since numerical aperture (N.A.) is given by:

$$N.A. = n\sin\left(\frac{\alpha_2}{2}\right)$$

the lateral extensions $\Delta r_i$ shows that for a large N.A., the focal spot is small. For a small N.A. the focal spot is relatively larger. These two values set the boundary value limits for the range of aperture sizes that should be designed for an embodiment of the present invention. In mathematical terms, the diameter of the aperture, a, should satisfy the following:

$$\frac{0.61\lambda}{\sin\left(\frac{\alpha_2}{2}\right)} > a > \frac{1.22\lambda}{\sin\left(\frac{\alpha_1}{2}\right)}$$

To control light reflected from the surface of the aperture plate 50, the two surfaces, 52 and 53, of FIG. 4 must be optically flat. With optically flat surfaces, the reflection of the light from the surfaces is predictable and thus, controllable. Thus, tilting of the aperture plate can direct undesired surface reflected light in a direction where such light is less harmful. The convenient placement of light stops or other light absorbing component in the direction of the controlled reflected light may minimize these interferences. To reduce interference between the two surfaces of the aperture plate 80, the two surfaces, 52 and 53, can be made unparallel to each other. Such a configuration is shown in FIG. 4.

Figure 6:
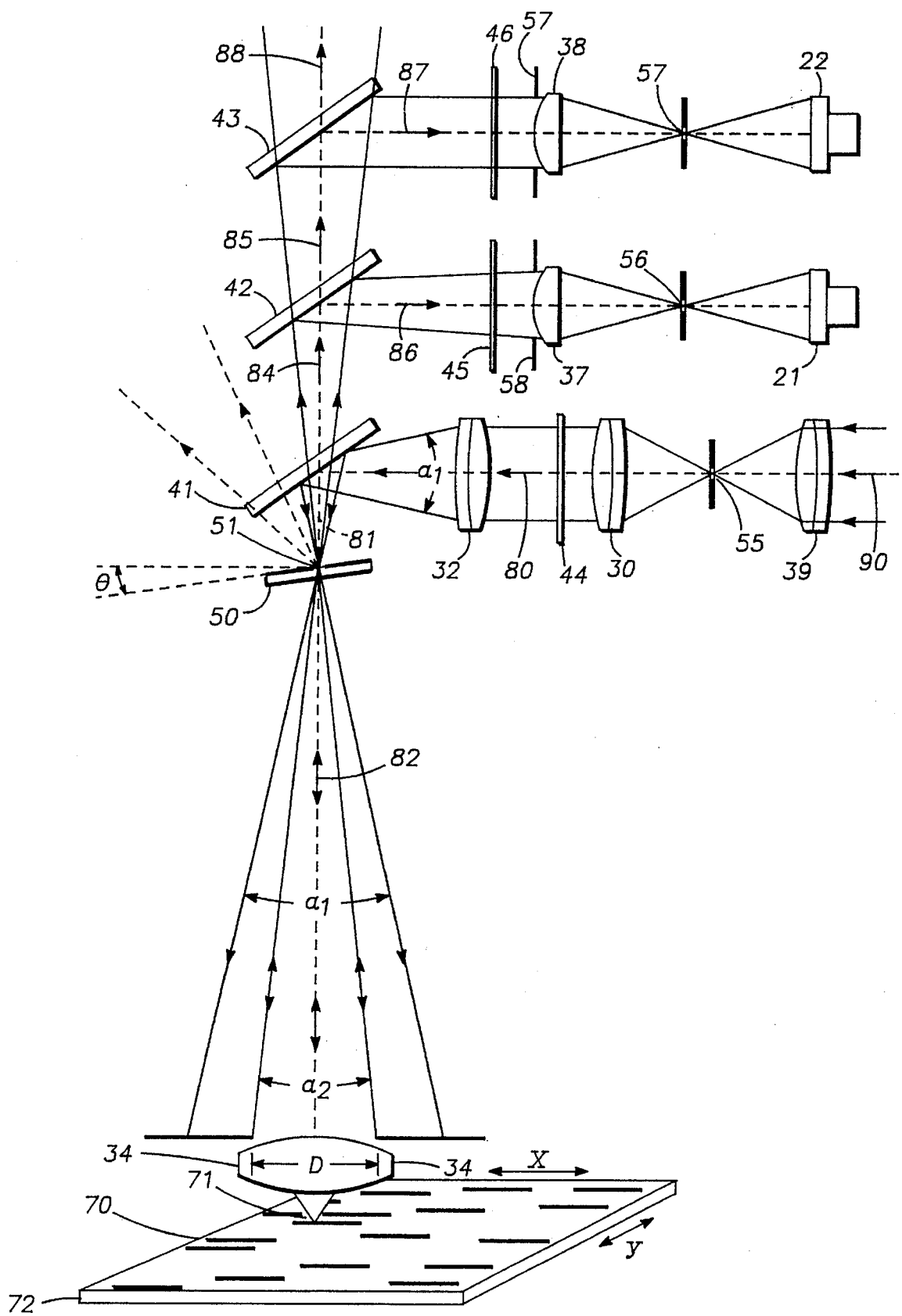
FIG. 6 shows another embodiment of the present invention in a confocal fluorescence scanner. In contrast to the embodiment of FIG. 2, the image point on the object is changed by moving the translation stage.

Anti-reflection coating may also be applied to various surfaces of the optical system to minimize negative effects from surface reflections. Opaque film, such as Chrome, on surface 52 of the aperture plate 50 may be further coated with an anti-reflection coating, such as Chrome Oxide or Chrome Nitride. The clear region on the patterned side and the opposite surface 53 of the aperture plate 50 should be coated with a broadband anti-reflection coating to reduce light loss through the substrate and to reduce multiple reflections of light or interference between the two opposite surfaces of the aperture plate FIG. 6 shows another embodiment of the present invention. As in FIG. 2, this embodiment is particularly suited as a confocal fluorescence scanner. Light 90 from the light source (not shown) such as a laser or arc lamp is first focused to light entrance aperture 55 with focusing lens 39. The light passing through the aperture 55 is then collimated by a collimating lens 30 and filtered by the excitation filter 44. Focusing lens 32 focuses the filtered light along path 80 toward dichroic mirror 41, which redirects the beam along path 81 to aperture 51 on aperture plate 50. The light passing through the aperture 51 is focused by an objective lens 34 to a image point 71 on object 70 containing fluorescent marked materials. The object 70 can be a fluorescence tagged nucleic acid or polypeptide in a gel slab or in capillary tubes.

The fluorescence light from the object 70 is collected by the objective 34 and is focused back onto the aperture plate along light path 82. The light returning back through the aperture 51 travels through dichroic mirror 41 along path 84. Dichroic mirror 42 splits the light into two paths 85 and 86 of different spectral composition. Similarly, dichroic minor 43 splits the light along light path 85 into light path 87 and 88. Several dichroic mirrors may be installed in a cascaded fashion, if desired, by placing them along light path 88. Light traveling along path 86, 87 encounter barrier filters 45, 46, respectively. Only light of desired range of wavelengths pass through the barrier filters 45 and 46. Lenses 37 and 38 focus the light from filters 45, 46 to light exit aperture 56, 57 and collected by sensors 21, 22. In each light path 86 or 87, either the dichroic mirrors 42, 43 or barrier filters 45, 46 or the two sets in combination determine the range of wavelengths that ultimately pass to the sensors 21, 22. Each sensor only detects light of limited range of wavelengths. So fluorescence light from the object 70 can be separated into its spectral constituents through the optical system and detected by sensors 21, 22. The relative intensity of the spectral constituents reveals the property of the object.

The object 70 may be mounted on a mechanical translation stage 72, which can move the object in the x, y, and z directions and hence change the location of the image point 71 on the object 70. Thus, unlike the embodiment of FIG. 2, no scanner is used. The object can be a fluorescence tagged nucleic acid or polypeptide in a gel slab or in capillary tubes. Scanning the sample relative to the image point 71 produces a map of the fluorescence properties of the object.

As discussed above, interference due to scattered and reflected light may be minimized by tilting the aperture plate, making the two major surfaces of the aperture plate optically flat, coating the aperture plate surfaces with -reflective coating, making the two major surfaces of the aperture plate unparallel, sizing the aperture properly, matching the entrance aperture and exit apertures with the aperture 51, and use of light stops 57, 58 to reject scattered light from aperture plate 50.

Although the embodiments disclosed herein described various optic conditioners to filter, condition, and focus light in various locations, a broader embodiment would utilize a set of focusing lenses to focus incident light in the aperture of the tilted aperture plate and the image point on the object, and focus return light in the same aperture and in the light exit aperture. The various filters and beam splitters are utilized for task specific applications such as fluorescence imaging.

Although the present invention has been described with reference to a particular embodiment, additional embodiments, applications, and modifications that are obvious to those skilled in the an or are equivalent to the disclosure are included within the spirit and scope of the invention. Therefore, this invention should not be limited to the specific embodiment discussed and illustrated herein, but rather by the following claims and equivalents thereof.

I claim:

1. A scanning confocal imaging system for imaging an object with light from a light source and detecting the image in a sensor, comprising:

an aperture means to pass incident light from the light source and return light from the object, the return light generated in response to the incident light illuminating the object, including:

an aperture plate with a first surface facing the incident light and a second surface facing the return light, and at least one aperture in the aperture plate, wherein the aperture plate is tilted at an angle from an imaginary plane, the imaginary plane lying normal to the incident and return light path;

an image position means to position an image point on any desired location on the object; and a beam splitter configured between the aperture means and the sensor for directing at least a portion of the return light toward the sensor.

2. A scanning confocal imaging system as in claim 1 wherein the image position means is a translation stage.

3. A scanning confocal imaging system as in claim 1 wherein the image position means is a scanner for directing incident light toward the image point on the object and redirecting the return light from the image point on the object toward the aperture, and a translation stage.

4. A scanning confocal imaging system as in claim 1 further comprising:

a light entrance aperture, wherein the light entrance aperture is matched to the aperture on the aperture plate; and a first optic conditioning means configured between the light entrance aperture and the object along a light path through the aperture for conditioning and focusing incident light to form a focused image plane in the aperture and on the object.

5. A scanning confocal imaging system as in claim 4 further comprising:

a light exit aperture, wherein the light exit aperture is matched to the aperture on the aperture plate; and a second optic conditioning means configured between the object and the light exit aperture along a light path through the aperture for conditioning and focusing return light to form and pass a focused image in the aperture and the light exit aperture.

6. A scanning confocal imaging system as in claim 5 further comprising:

an entrance optical fiber to guide the incident light from the light source to the light entrance aperture; and an exit optical fiber to guide the return light from the light exit aperture to the sensor.

7. A scanning confocal imaging system as in claim 1 wherein the aperture on the aperture plate is a pinhole.

8. A scanning confocal imaging system as in claim 1 wherein the aperture on the aperture plate is a slit.

9. A scanning confocal imaging system as in claim 5 wherein the first optic conditioning means includes a focusing lens, and the second optic conditioning means includes a focusing lens.

10. A scanning confocal imaging system as in claim 1 wherein the aperture means further includes an anti-reflection material coated on the first surface and the second surface.

11. A scanning confocal imaging system as in claim 1 wherein the aperture means further includes a transparent aperture plate, an opaque film coated on the first surface, and the opaque film is not coated on the aperture region of the aperture plate.

12. A scanning confocal imaging system as in claim 5 wherein at least one light stop is configured between the light exit aperture and the aperture plate to block reflected light from either surface of the aperture plate.

13. A scanning confocal imaging system as in claim 1 wherein the first surface and the second surface are optically flat.

14. A scanning confocal imaging system as in claim 1 wherein the first surface and the second surface are not parallel to each other.

15. A scanning confocal imaging system as in claim 1 wherein the size of the aperture allows all of the incident light to pass through in the direction of the incident light but allows only a portion of the return light to pass through in the direction of the return light.

16. A scanning confocal imaging system as in claim 5 wherein the first optic conditioning means includes an excitation filter and a focusing lens, the second optic conditioning means includes a barrier filter and a focusing lens, and the beam splitter is a dichroic mirror.

17. A scanning confocal imaging system as in claim 1 wherein the aperture plate is tilted at an angle such that the first surface is not normal to the incident light path or the second surface is not normal to the return light path.

18. A scanning confocal imaging system as in claim 16 wherein the object is a fluorescence tagged nucleic acid or polypeptide in a gel slab or in capillary tubes.

19. A method of obtaining focal images from a single aperture confocal imaging system, comprising the steps:

generating incident light with a light source to illuminate a focal image point on an object, which in turn generates return light;

conditioning and focusing incident light toward an aperture in an aperture plate having two major surfaces;

tilting the aperture plate so as to pass incident and return light and redirecting reflected light from the two major surfaces in a direction not parallel to the incident and return light path;

conditioning and focusing return light toward the aperture;

directing the return light into a sensor; and detecting at least a portion of the focal image in the return light.

20. A method of obtaining focal images from a single aperture confocal imaging system as in claim 19 further comprising the steps:

focusing and conditioning return light from the aperture to the detector;

transforming the return light; and detecting the transformed return light.

21. A method of obtaining focal images from a single aperture confocal imaging system as in claim 20 wherein the return light is transformed by converting the wavelength of the return light to another wavelength or range of wavelengths.

22. A method of obtaining focal images from a single aperture confocal imaging system as in claim 19, further comprising the steps:

sizing the aperture large enough to pass incident light and a substantial portion of return light, and small enough to pass a minimal mount of scattered light; and coating the two major surfaces of the aperture plate with anti-reflection coating.

23. A method of obtaining focal images from a single aperture confocal imaging system as in claim 22, further comprising the step:

configuring a light stop at a final aperture at an input to a detector; and configuring a light stop in the directions of the light reflected from the two major surfaces of the aperture plate.

24. A scanning confocal imaging system for imaging an object with light from a light source and detecting the image in a sensor, comprising:

an aperture means to pass incident light from the light source and return light generated in response to the incident light illuminating the object, including:

an aperture plate with a first surface facing the incident light and a second surface facing the return light, and at least one aperture in the aperture plate, wherein the aperture is of such size as to allow all of the incident light to pass through in the direction of the incident light but allow only a portion of the return light to pass through in the direction of the return light;

an image position means to position an image point on any desired location on the object; and a beam-splitter configured between the aperture means and the sensor for directing at least a portion of the return light toward the sensor.

25. A scanning confocal imaging system as in claim 24 wherein the image position means is a translation stage.

26. A scanning confocal imaging system as in claim 24 wherein the image position means is a scanner for directing incident light toward the image point on the object and redirecting the return light from the image point on the object toward the aperture, and a translation stage.

27. A scanning confocal imaging system as in claim 24 further comprising:

a light entrance aperture, wherein the light entrance aperture is matched to the aperture on the aperture plate; and a first optic conditioning means configured between the light entrance aperture and the object along a light path through the aperture for conditioning and focusing incident light to form a focused image plane in the aperture and on the object.

28. A scanning confocal imaging system as in claim 27 further comprising:

a light exit aperture, wherein the light exit aperture is matched to the aperture on the aperture plate; and a second optic conditioning means configured between the object and the light exit aperture along a light path through the aperture for conditioning and focusing return light to form and pass a focused image in the aperture and the light exit aperture.

29. A scanning confocal imaging system as in claim 28 further comprising:

an entrance optical fiber to guide the incident light from the light source to the light entrance aperture; and an exit optical fiber to guide the return light from the light exit aperture to the sensor.

* * * * *